(12) United States Patent
Inoue

(10) Patent No.: US 8,737,566 B2
(45) Date of Patent: May 27, 2014

(54) X-RAY IMAGING SYSTEM, X-RAY IMAGING METHOD, AND STORAGE MEDIUM

(75) Inventor: Hitoshi Inoue, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/483,616

(22) Filed: May 30, 2012

(65) Prior Publication Data

US 2012/0307975 A1  Dec. 6, 2012

(30) Foreign Application Priority Data

Jun. 3, 2011 (JP) .................... 2011-125250

(51) Int. Cl.
*H05G 1/08* (2006.01)
(52) U.S. Cl.
USPC ............................................. 378/91; 378/98.8
(58) Field of Classification Search
USPC .................. 378/98, 98.8, 91; 250/370.09
See application file for complete search history.

(56) References Cited

U.S. PATENT DOCUMENTS

| 7,289,033 B2 * | 10/2007 | Hockersmith ............. 378/4 |
| 2009/0032745 A1 * | 2/2009 | Kito et al. ............. 250/582 |
| 2010/0187427 A1 * | 7/2010 | Kuwabara et al. ....... 250/370.08 |
| 2012/0250825 A1 * | 10/2012 | Yoshida et al. ............. 378/91 |

FOREIGN PATENT DOCUMENTS

JP  3494683 B2  6/1995

* cited by examiner

*Primary Examiner* — Glen Kao
(74) *Attorney, Agent, or Firm* — Canon USA Inc. IP Division

(57) ABSTRACT

An X-ray imaging system includes an X-ray image receiving unit configured to convert a spatial intensity distribution of X-ray radiation which has passed through a subject into image data, a wireless base station configured to perform wireless communication with the X-ray image receiving unit, and a control unit configured to limit a communication possible range of the wireless base station when imaging by the X-ray image receiving unit is controlled with respect to the communication possible range when image data captured by the X-ray image receiving unit is communicated.

24 Claims, 7 Drawing Sheets

X-RAY IMAGING SYSTEM, X-RAY IMAGING METHOD, AND STORAGE MEDIUM

BACKGROUND OF THE INVENTION

1. Field of the Invention

The present invention relates to an X-ray imaging system suitable for medical and non-medical imaging, more in particular the present invention relates to an X-ray imaging system and wireless communications therefor.

2. Description of the Related Art

Currently, digital X-ray images are used for examining an internal structure of a human body or a subject. Such images are spatial distribution images of X-ray intensity passing through the subject. In the field of medical care and non-destructive inspection, a flat panel semiconductor imaging device (flat panel detector (FPD)) is used for obtaining a digital image used for examining the inside of a comparatively large object such as a human body. By using the FPD, a digital X-ray image, which is a digitized image of the X-ray intensity distribution, is obtained.

A digital image is generally characterized by an accurate and high-speed transmission of image information without damaging it. As typified by the technique of wireless local area network (LAN), which has developed rapidly during recent years, image data acquired by the FPD can be transmitted to a computer system by wireless transmission for purposes such as observation, storage, and management of the image data.

A difficult part of imaging an inside of a large object (subject) by using an X-ray beam is to set the subject between an X-ray source and the FPD. Generally, since the allowable movement range of the subject is small when the subject is large, the positions of the X-ray source and the FPD are changed so that the subject can be set between them.

Since it is necessary to set the FPD close to the subject, the FPD needs to be provided with a greater degree of flexibility when its position is changed than when it is not. For example, if a power control cable or an image transmission cable is connected to the FPD, the freedom of the FPD, when its position is changed, is reduced. Thus, an FPD using wireless connections (hereinafter referred to as a wireless FPD) is attracting attention. According to the progress in the technique of wireless LAN that aids in stable digital communication, the wireless FPD is close to practical use.

In addition to the high degree of flexibility in the selection of an imaging position, the wireless FPD is characterized by its flexibility in the determination of a utilization site. For example, even if a plurality of X-ray sources is provided in a plurality of rooms or locations, a plurality of wireless FPDs are not necessary. In other words, a single wireless FPD can be carried to the room or the location of each X-ray source and used. Accordingly, usability of the comparatively expensive wireless FPD can be improved.

FIG. 7 illustrates an example of X-ray imaging performed by two X-ray systems A and B. Each of X-ray sources 101 and 102 includes an X-ray tube and a collimator. High voltage control devices 103 and 104 are for X-ray generation. Each of X-ray interfaces 105 and 106 controls the high voltage control device to generate pulsed X-rays. Each of access points (APs) 107 and 108 is a wireless base station of a wireless LAN and is used for controlling the X-ray interface by wireless communication. In FIG. 7, imaging of a subject 110 is performed by the X-ray system B by using a wireless FPD 109.

One feature of the X-ray control is to generate an X-ray pulse in synchronization with a driving operation of the FPD. Thus, immediacy is required in the transmission of a control system. Normally, one AP for wireless FPD is uniquely determined for each X-ray system. To be more precise, immediate and stable control is realized according to the provision of the dedicated APs 107 and 108 for the X-ray systems A and B, respectively.

Whether to use the X-ray system A or B is set in advance before the wireless FPD 109 is used. Thus, the wireless FPD 109 is connected to either the AP 107 or 108 by wireless communication and not connected to both APs. Further, since the wireless FPD cannot include a plurality of wireless communication devices, image data is generally transmitted via the AP used for the X-ray control.

Japanese Patent No. 3494683 discusses a technique useful for solving the issues below.

Radio waves of wireless LAN can cover a comparatively wide range. Thus, as illustrated in FIG. 7, even if a user desires to perform imaging by the X-ray system B, actually the X-ray system A may be connected to the wireless FPD 109.

For example, even if the user sets the wireless FPD 109 in the vicinity of the X-ray system B, since it is the X-ray system A that is connected to the wireless FPD 109 by wireless connection, the user may perform the X-ray irradiation by using the X-ray system B, which is not connected to the wireless FPD 109, when the communication with the AP 107 is established. In this case, either the X-ray is not emitted from the X-ray system B or the X-ray is emitted but not in synchronization with the wireless FPD. Accordingly, normal X-ray imaging cannot be performed.

In order to prevent such an issue from occurring, for example, the user needs to change the setting of the wireless connection so that the X-ray system B can be used. However, when the user moves the FPD to a different location, the user tends to forget to change the setting of the wireless connection.

One of the resolution methods of such a case focuses on the distance between the X-ray source, which includes the X-ray tube and the collimator, and the wireless FPD. For example, since the X-ray imaging is generally performed by close-range imaging (normally 1 to 3 meters), whether the distance between the wireless FPD and the X-ray tube is within a distance defined in normal X-ray imaging can be used in the determination. In this case, by setting an AP that communicates with the wireless FPD at the X-ray tube or the collimator and limiting an allowable range of the wireless communication, the issue can be easily solved.

However, the original purpose of using a wireless device in the wireless FPD is to transmit the image data obtained by the wireless FPD. Thus, the intended purpose of the wireless device is not limited to confirming the correct wireless connection by setting an AP at the position of the X-ray tube, limiting the distance of the wireless communication, and substantially matching the distance of the wireless communication with the distance of the X-ray imaging.

The important thing is to reliably transmit the captured image data even if the wireless FPD is moved to a different location after imaging and, further, even if it is not at a location not appropriate for imaging. In other words, imaging with connection to the correct X-ray tube, which is realized by limiting the distance between the AP and the FPD for the wireless communication, is required as well as reliably transmitting the obtained image data regardless of the distance after imaging.

SUMMARY OF THE INVENTION

The present invention is directed to easily determining a correct combination of an X-ray tube and a wireless FPD and realizing stable data transfer of obtained image data.

According to an aspect of the present invention, an X-ray imaging system includes an X-ray image receiving unit configured to convert a spatial intensity distribution of X-ray radiation which has passed through a subject into image data, a wireless base station configured to perform wireless communication with the X-ray image receiving unit, and a control unit configured to limit a communication possible range of the wireless base station when imaging by the X-ray image receiving unit is controlled with respect to the communication possible range when image data captured by the X-ray image receiving unit is communicated.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE EMBODIMENTS

Various exemplary embodiments, features, and aspects of the invention will be described in detail below with reference to the drawings.

Figure 1:
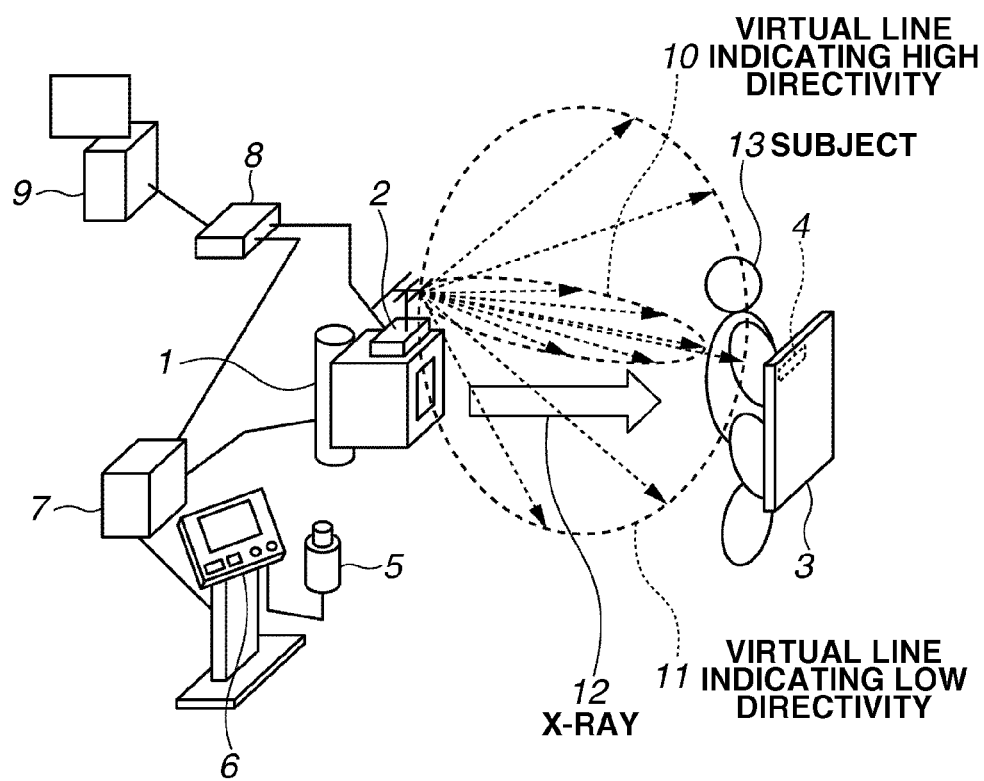
FIG. 1 illustrates a configuration example of an X-ray imaging system according to an exemplary embodiment of the present invention.

First, a first exemplary embodiment of the present invention will be described. FIG. 1 illustrates a configuration example of an X-ray imaging system according to the first exemplary embodiment of the present invention.

In FIG. 1, an X-ray tube 1, which is an X-ray source emitting an X-ray, emits the X-ray in the direction of an arrow 12 by an X-ray collimator, which is an X-ray diaphragm controlling an irradiation range of the X-ray. The emitted X-ray passes through a subject 13 such as a human body. Then, an X-ray two-dimensional spatial intensity distribution that expresses an internal structure of the subject by the difference of the amount of transmission of the X-ray is detected as an electric signal by an X-ray image receiving device (FPD) 3. The FPD 3 internally includes a wireless LAN communication device 4, and synchronizes the X-ray irradiation timing and the X-ray reception timing to transmit obtained X-ray image data by the wireless LAN communication device 4.

An AP 2 is a wireless base station of a wireless LAN. The AP 2 is set at the position of the X-ray tube 1 and performs wireless communication with the wireless LAN communication device 4 in the FPD 3. By the AP 2 communicating with the wireless LAN communication device 4, the X-ray irradiation timing is in synchronization with the X-ray reception timing. Further, the AP 2 receives the obtained X-ray image data.

As an AP of the wireless LAN, only an antenna may be set at the position of the AP. An X-ray generation timing control interface 8 is connected to an X-ray generation high-voltage generation device 7 and controls the timing of the X-ray irradiation. The X-ray generation timing control interface 8 is also connected to the AP 2 of the wireless LAN and synchronizes the X-ray irradiation timing and the X-ray reception timing.

Further, the X-ray generation timing control interface 8 transmits the X-ray image data obtained from the FPD via the AP 2 of the wireless LAN to an imaging control computer 9. The imaging control computer 9 controls the whole X-ray imaging operation by using a program unit in the computer. The obtained X-ray image data is stored in a data storage unit in the imaging control computer 9 together with information of the subject (patient information) and an X-ray imaging condition.

Further, the program unit in the imaging control computer 9 can control a radio wave state of the AP 2 of the wireless LAN via the X-ray generation timing control interface 8. The control of the radio wave state is to control the directivity of the radio wave output from the AP 2.

The purpose of controlling the directivity is to determine whether the wireless communication unit (FPD) is located within a predetermined communication possible range from the access point. Normally, the distance between the X-ray tube and the FPD is within a range of 1 to 3 meters and the width of the FPD is approximately 40 cm.

Considering these geometric relationships (distance: 1 m and width: 40 cm), whether the FPD is located at an appropriate position is determined by increasing the directivity. At this time, the desirable angle of directivity is approximately 20 degrees or lower. The directivity is changed by preparing an antenna with high directivity and a normal antenna with low directivity. Then, the directivity is changed by changing the power source.

The X-ray is generated by the X-ray generation high-voltage generation device 7 providing a high voltage to the X-ray tube 1. Further, the X-ray generation high-voltage generation device 7 is connected to an X-ray generation control console 6. The user sets the X-ray irradiation condition (e.g., voltage/current provided to the X-ray tube (X-ray tube voltage/X-ray tube current) and X-ray duration (X-ray pulse duration) via this console.

An X-ray irradiation instruction button 5 is attached to the X-ray generation control console 6. The X-ray is irradiated when the user presses the X-ray irradiation instruction button 5 after setting the irradiation condition of the X-ray.

The wireless LAN communication device 4 and the AP 2 of the wireless LAN are matched by a unit (not illustrated) so that they can communicate with each other. Thus, they have a matching wireless communication method, a matching communication frequency (channel), and a matching decryption keyword. The settings of the wireless LAN communication device 4 and the AP 2 are such that, if they are arranged within a communication possible distance, they can communicate with each other in that state.

In FIG. 1, a virtual line 10 is a line schematically indicating the directivity of the radio wave transmitted from the AP of the wireless LAN. The virtual line 10 shows high directivity in the same direction as the X-ray irradiation direction. Further, a virtual line 11 is a line indicating low directivity of the radio wave from the AP, and the AP 2 of the wireless LAN can communicate with the wireless LAN communication device 4 in a wide range.

An operation of the present embodiment will be described below. An operator sets the X-ray tube 1 and the FPD 3 so that they face each other and makes the subject 13 to stand between them. Then, the operator presses the X-ray irradiation instruction button 5 and obtains the X-ray image data. The timing at which the operator presses the button is transmitted to the imaging control computer 9 via the X-ray generation high-voltage generation device 7 and the X-ray generation timing control interface 8.

A subsequent operation of the computer program will now be described with reference to the flowchart illustrated in FIG. 2.

In step S201, the imaging control computer 9 determines whether the above-described X-ray irradiation instruction button 5 has been pressed. If the X-ray irradiation instruction button 5 has been pressed (YES in step S201), the processing proceeds to step S202. If the X-ray irradiation instruction button 5 has not been pressed yet (NO in step S201), the processing returns to step S201. In step S202, the imaging control computer 9 controls the radio wave state of the AP 2 of the wireless LAN so that the radio wave of the AP 2 has high directivity in the direction of the X-ray irradiation. In step S203, the imaging control computer 9 evaluates the state of communication between the AP 2 of the wireless LAN and the wireless LAN communication device 4 in the FPD 3 based on the information transmitted from the AP 2 of the wireless LAN.

The evaluation is based on, for example, whether the following conditions are satisfied:

Perform trial data communication and determine whether the radio field intensity of the radio waves received by the AP 2 and the wireless LAN communication device 4 is above a predetermined value.

Perform trial data communication and determine whether the overall data communication speed (bit/second) considering re-transmission of data due to transmission error is above a predetermined value.

In step S204, the imaging control computer 9 determines whether the communication is established according to, for example, the conditions described above. If the communication is not yet established, since the communication is not established under high directivity, the imaging control computer 9 determines that the position of the FPD 3 in FIG. 1 is not appropriate for the X-ray imaging (not within the communication possible range). Thus, if the communication is not yet established (NO in step S204), the processing proceeds to step S209 and the X-ray irradiation stops. In step S209, a warning message is displayed on a display unit of the computer to warn the user that the X-ray irradiation has stopped.

On the other hand, if the communication is established in step S204 (YES in step S204), the processing proceeds to step S205. In step S205, X-ray irradiation permission information is transmitted to the X-ray generation high-voltage generation device 7 via the X-ray generation timing control interface 8 in FIG. 1. The X-ray generation high-voltage generation device 7 applies a high voltage to the X-ray tube 1 when it receives the permission information. Then the X-ray is emitted.

Figure 2:
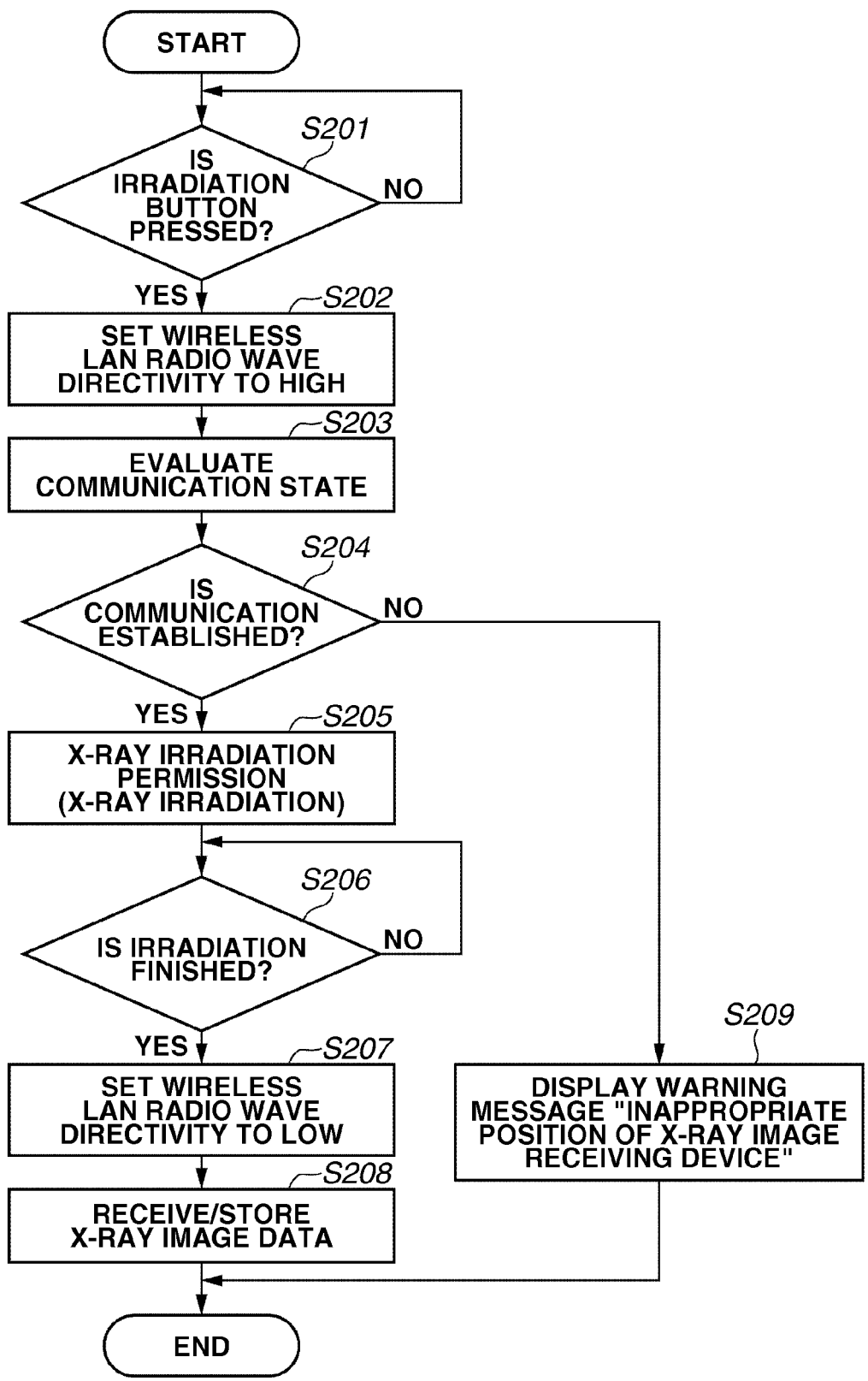
FIG. 2 is a flowchart illustrating an operation of the X-ray imaging system according to an exemplary embodiment of the present invention.

In step S206 in FIG. 2, the imaging control computer 9 monitors the state of the X-ray irradiation and determines whether the irradiation is finished. If the X-ray irradiation is finished (YES in step S206), the processing proceeds to step S207. The processing in step S207 is to reliably transmit the X-ray image data regardless of the location of the FPD. Thus, in step S207, the imaging control computer 9 sets the directivity of the radio wave of the AP 2 of the wireless LAN to low and cancels the limits on the communication possible range so that a wide-range communication is possible. Accordingly, the data is reliably stored in the data storage unit in the imaging control computer 9.

Thus, the operator can carry the FPD to a different location in a comparatively free manner while transferring the data immediately after the imaging. If the positional relation of the X-ray source and the FPD is confirmed according to the communication state determination in step S203, the processing in step S207 can be performed before the X-ray irradiation.

Although the directivity of the AP of the wireless LAN is changed according to the present embodiment, the directivity of a wireless LAN device in the FPD can also be changed. Further, a similar effect can be obtained by simultaneously changing the directivity of both the AP and the wireless LAN device.

Next, a second exemplary embodiment of the present invention will be described.

According to the flowchart of the first exemplary embodiment illustrated in FIG. 2, the timing at which the wireless LAN radio wave directivity is set to "high" in step S202 is immediately after the X-ray irradiation instruction button 5 is pressed. However, as illustrated in the flowchart in FIG. 3, the wireless LAN radio wave directivity can be set to "high" before the X-ray irradiation instruction button 5 is pressed.

Figure 3:
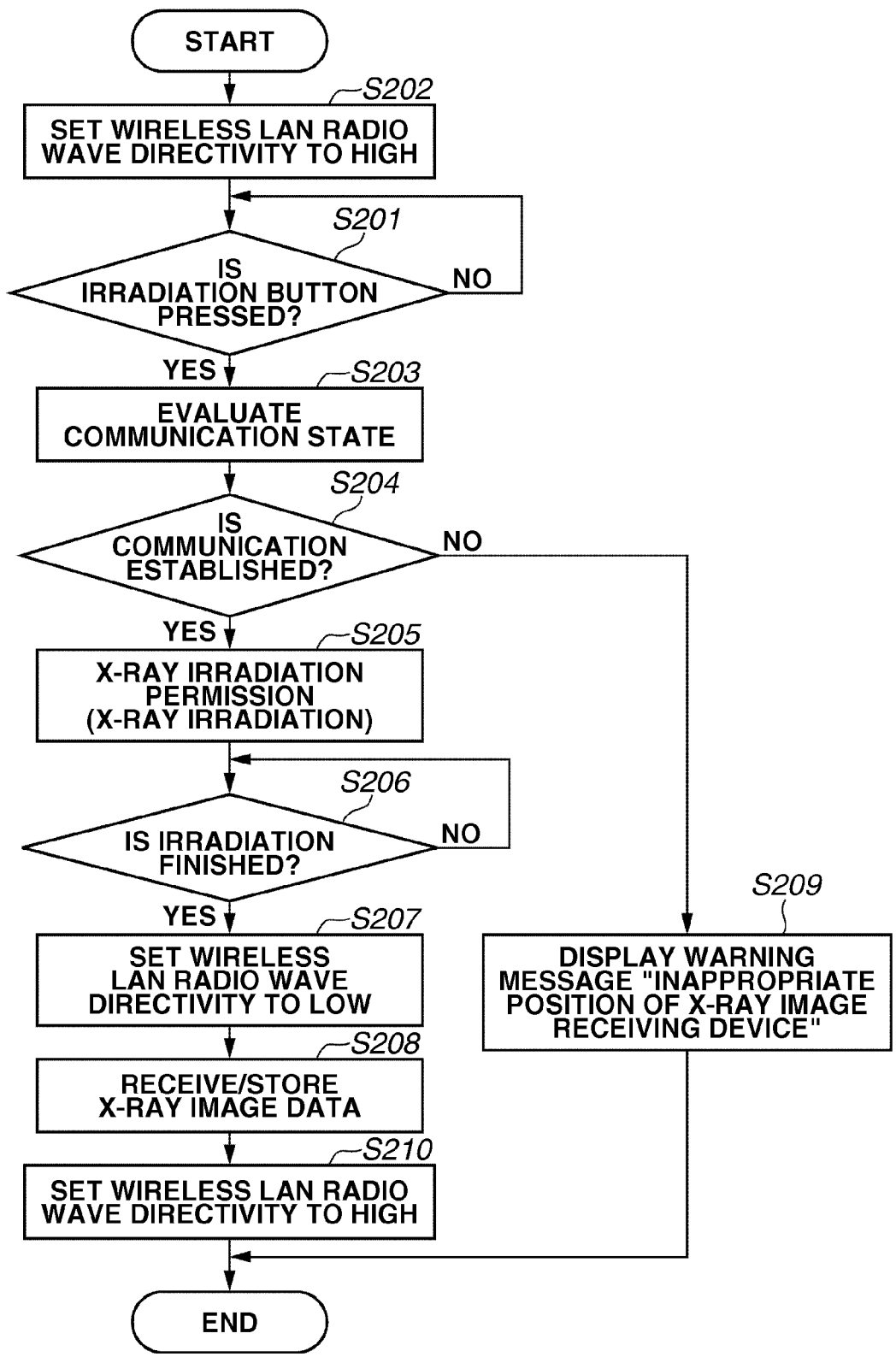
FIG. 3 is a flowchart illustrating an operation of the X-ray imaging system according to an exemplary embodiment of the present invention.

Further, in FIG. 3, as processing in steps S207, S208, and S210 indicates, since the data is received immediately after the X-ray irradiation is finished, the directivity is set to "low". The setting can be reset to "high" again when the reception of the X-ray image data is finished. In this case, the directivity is always set to "high" unless the image data is being received.

Then, a third exemplary embodiment of the present invention will be described. According to the first and the second exemplary embodiments, the directivity of the radio wave is changed before or after the X-ray irradiation. According to the present embodiment, an effect similar to changing the directivity is obtained by changing the intensity of the radio field.

Figure 4:
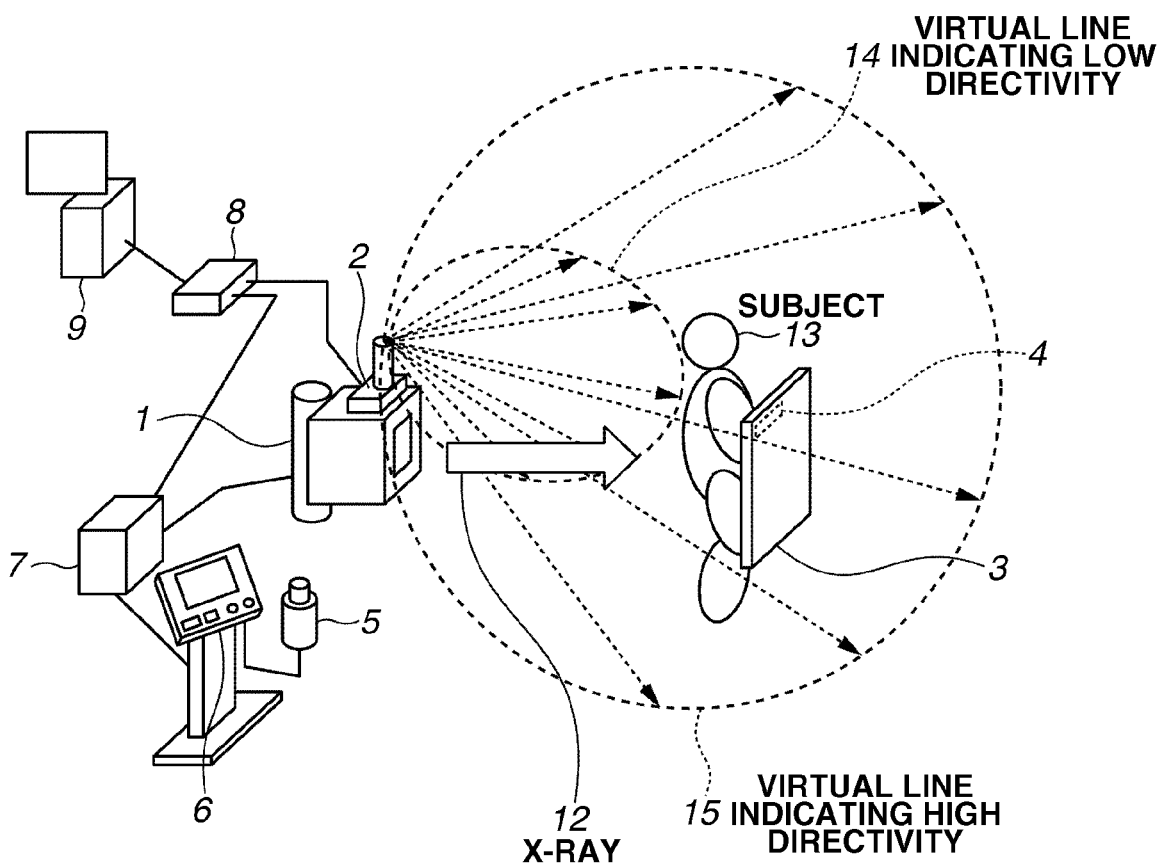
FIG. 4 illustrates a configuration example of the X-ray imaging system according to an exemplary embodiment of the present invention.

FIG. 4 illustrates the X-ray imaging system according to the third exemplary embodiment. FIG. 4 is basically similar to the X-ray imaging system in FIG. 1 except that it includes radio field intensity 14 and radio field intensity 15. The radio field intensity is low regarding the radio field intensity 14 and high regarding the radio field intensity 15.

The distance between the X-ray tube 1 and the FPD is set to 1 to 2 meters for the normal X-ray imaging. Thus, to set the radio field intensity to "low" is to adjust the intensity of the radio wave output from the wireless LAN arranged at the location of the X-ray tube 1 so that the distance which the radio wave reaches is approximately 2 meters.

The definition of the distance which the radio wave reaches described above does not simply mean a distance which the radio wave physically reaches but is a distance that enables established communication according to sufficient radio field intensity. To be more precise, the radio field intensity is greater than a predetermined value or an overall transmission speed (bit/second) of information, including re-transmission of data due to transmission error, is equal to or greater than a predetermined value.

The setting of the radio field intensity of the AP of the wireless LAN can be set by a command instruction issued by the imaging control computer 9. The AP of the wireless LAN that received the command adjusts the power supplied to the antenna. Accordingly, the intensity of the radio field can be set to high/low.

Figure 5:
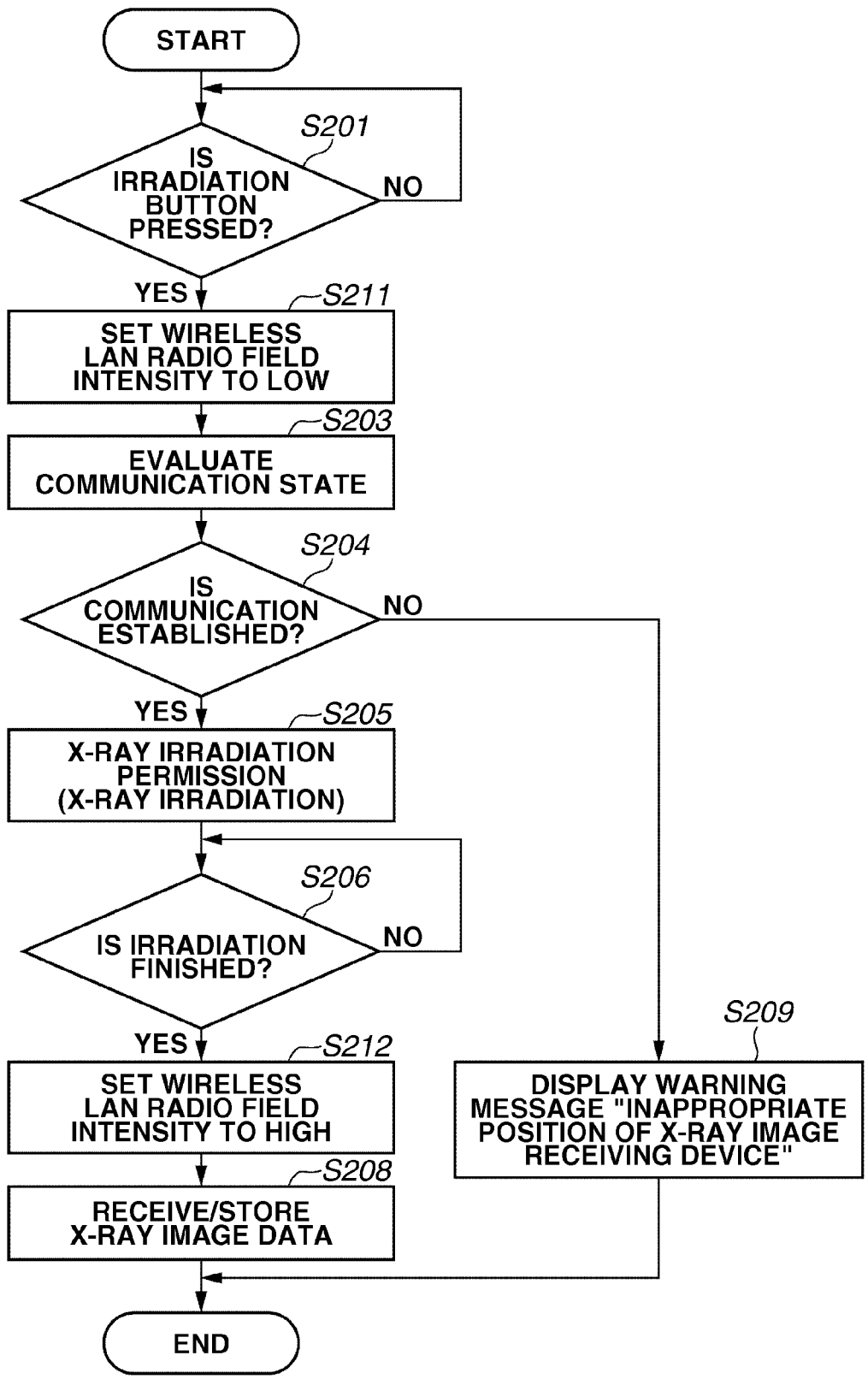
FIG. 5 is a flowchart illustrating an operation of the X-ray imaging system according to an exemplary embodiment of the present invention.

FIG. 5 is a flowchart illustrating an operation of the present embodiment. FIG. 5 is similar to the flowchart in FIG. 2.

If the X-ray irradiation instruction button 5 is pressed in step S201 (YES in step S201), the processing proceeds to step S211. In step S211, the imaging control computer 9 sets the radio field intensity of the wireless LAN to "low". In step S203, the imaging control computer 9 evaluates the state of communication between the AP 2 of the wireless LAN and the wireless LAN communication device 4 in the FPD 3 and determines whether the FPD is set at an appropriate position with respect to the X-ray tube 1.

The evaluation is based on, for example, whether the following conditions are satisfied:

Perform trial data communication and determine whether the radio field intensity of the radio waves received by the FPD is above a predetermined value.

Perform trial data communication and determine whether the overall data communication speed (bit/second) considering re-transmission of data due to transmission error is above a predetermined value.

In step S204, the imaging control computer 9 determines whether the communication is established. If the communication is established in step S204 (YES in step S204), the processing proceeds to step S205. In step S205, X-ray irradiation permission information is transmitted to the X-ray generation high-voltage generation device 7 via the X-ray generation timing control interface 8 in FIG. 4. The X-ray generation high-voltage generation device 7 applies a high voltage to the X-ray tube 1 when it receives the permission information. Then the X-ray is emitted.

In step S206 in FIG. 5, the imaging control computer 9 monitors the state of the X-ray irradiation and determines whether the irradiation is finished. If the X-ray irradiation is finished (YES in step S206), the processing proceeds to step S212. The processing in step S212 is to reliably transmit the X-ray image data regardless of the location of the FPD. Thus, in step S212, the imaging control computer 9 sets the radio field intensity of the AP of the wireless LAN to "high" so that the radio wave can be used in a wide range. Accordingly, the data is reliably stored in the data storage unit in the imaging control computer 9.

Thus, the operator can carry the FPD to a different location in a comparatively free manner while transferring the data immediately after the imaging. If the positional relation of the X-ray source and the FPD is confirmed according to the communication state determination in step S203, the processing in step S212 can be performed before the X-ray irradiation.

Although the radio field intensity of the AP of the wireless LAN is changed according to the present embodiment, the radio field intensity of the wireless LAN device in the FPD can also be changed. Further, a similar effect can be obtained by simultaneously changing the radio field intensity of both the AP and the wireless LAN device.

Finally, a fourth exemplary embodiment of the present invention will be described.

According to the flowchart of the third exemplary embodiment illustrated in FIG. 5, the timing the radio field intensity of the wireless LAN is set to "low" in step S211 is immediately after the X-ray irradiation instruction button 5 is pressed. However, as illustrated in the flowchart in FIG. 6, the radio field intensity of the wireless LAN can be set to "low" before the X-ray irradiation instruction button 5 is pressed.

Figure 6:
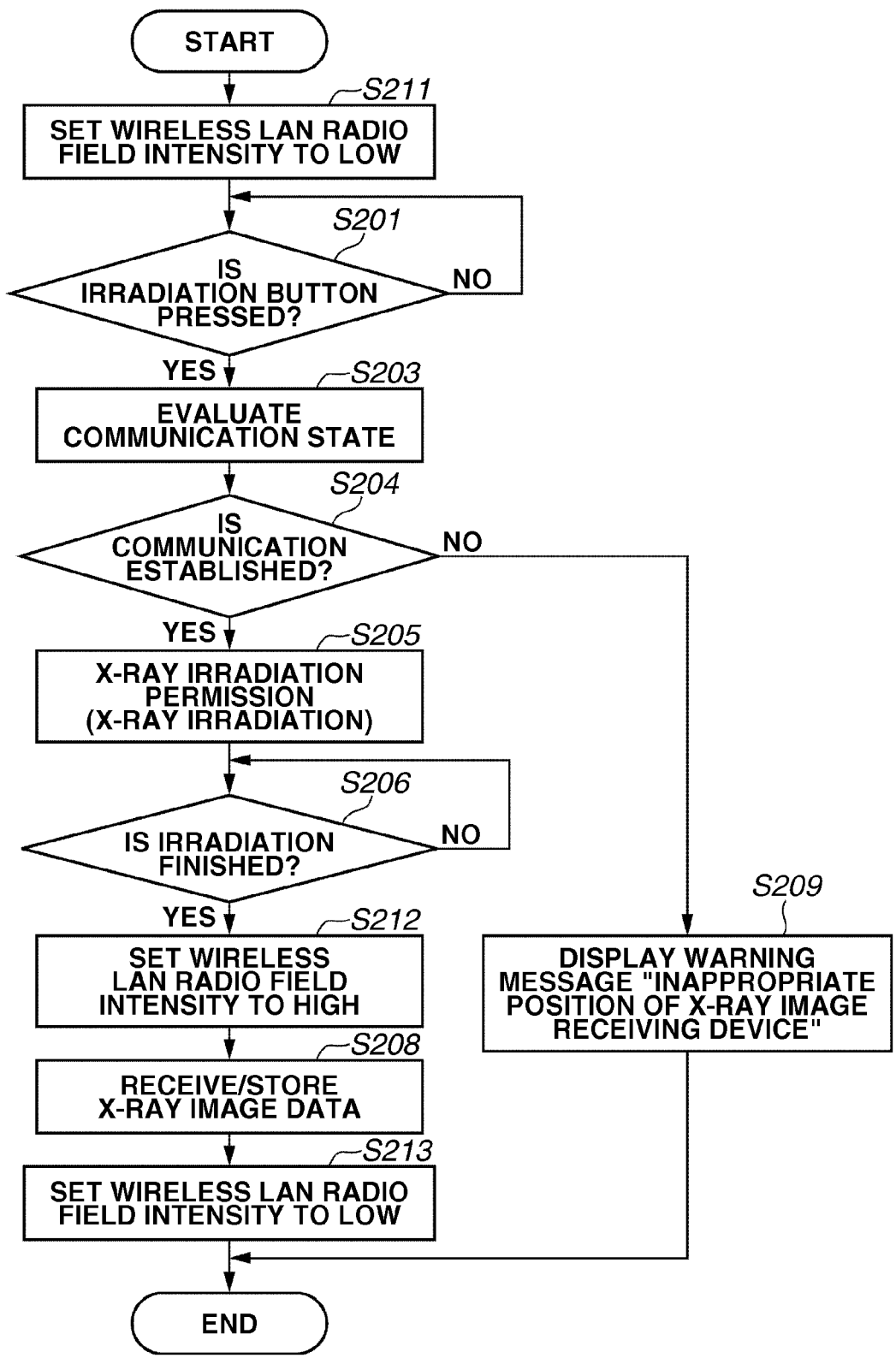
FIG. 6 is a flowchart illustrating an operation of the X-ray imaging system according to an exemplary embodiment of the present invention.
Figure 7:
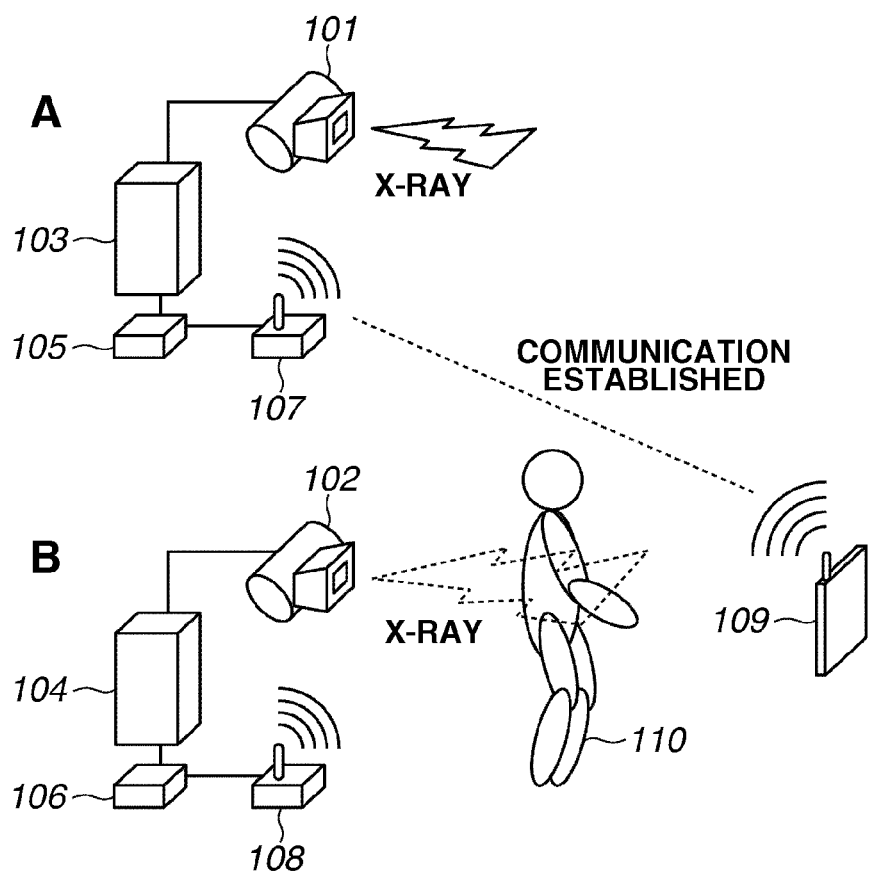
FIG. 7 illustrates an example of X-ray imaging performed according to a conventional technique.

Further, in FIG. 6, as processing in steps S212, S208, and S213 indicates, since the data is received immediately after the X-ray irradiation is finished, after the radio field intensity of the wireless LAN is set to "high" and the reception of the X-ray image is finished, the setting of the radio field intensity of the wireless LAN can be set to "low" again. In this case, the setting of the radio field intensity of the wireless LAN is always set to "low" unless the image data is being received.

Further, the above-described exemplary embodiments can also be achieved by supplying a software program that realizes each function of the aforementioned exemplary embodiments to a system or an apparatus via a network or various types of storage media, and a computer (or a CPU or a MPU) in the system or the apparatus reads and executes the program stored in such storage media.

As described above, according to the present invention, the correct combination of the X-ray tube and the wireless FPD can be easily confirmed and stable transfer of image data can be performed.

Aspects of the present invention can also be realized by a computer of a system or apparatus (or devices such as a CPU or MPU) that reads out and executes a program recorded on a memory device (computer-readable medium) to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium). In such a case, the system or apparatus, and the recording medium where the program is stored, are included as being within the scope of the present invention.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-125250 filed Jun. 3, 2011, which is hereby incorporated by reference herein in its entirety.

What is claimed is:

1. An X-ray imaging system comprising:
an X-ray image receiving unit configured to convert a spatial intensity distribution of X-ray radiation which has passed through a subject into image data;
a wireless base station configured to perform wireless communication with the X-ray image receiving unit; and
a control unit configured to limit a communication possible range of the wireless base station when imaging by the X-ray image receiving unit is controlled with respect to the communication possible range when image data captured by the X-ray image receiving unit is communicated.

2. The X-ray imaging system according to claim 1, wherein the communication possible range is a range where an intensity of a radio wave received by the wireless base station or the X-ray image receiving unit is equal to or greater than a predetermined value.

3. The X-ray imaging system according to claim 1, wherein the communication possible range is a range where an amount of information correctly communicated in a given length of time is equal to or greater than a predetermined value.

4. The X-ray imaging system according to claim 1, wherein limiting the communication possible range is to limit directivity of a radio wave of the wireless base station or the X-ray image receiving unit.

5. The X-ray imaging system according to claim 1, wherein limiting the communication possible range is to limit a communication possible distance by lowering an intensity of a radio wave of the wireless base station or the X-ray image receiving unit.

6. The X-ray imaging system according to claim 1, wherein the control unit is further configured to cancel limiting of the communication possible range after X-ray imaging is performed.

7. The X-ray imaging system according to claim 1, wherein, in a case where communication with the X-ray image receiving unit on a predetermined condition cannot be performed when the control unit limits the communication possible range of the wireless base station, a warning is displayed on a display unit.

8. A control method for an X-ray image receiving unit configured to convert a spatial intensity distribution of X-ray radiation which has passed through a subject into image data and a wireless base station configured to perform wireless communication with the X-ray image receiving unit, the control method comprising:
limiting a communication possible range of the wireless base station when imaging by the X-ray image receiving unit is controlled with respect to the communication possible range when image data captured by the X-ray image receiving unit is communicated.

9. A non-transitory computer-readable storage medium storing a program causing a computer to execute a control method for a wireless base station configured to perform wireless communication with an X-ray image receiving unit, the control method comprising,
limiting a communication possible range of the wireless base station when imaging by the X-ray image receiving unit is controlled with respect to the communication possible range when image data captured by the X-ray image receiving unit is communicated.

10. An X-ray imaging system comprising:
an X-ray image receiving unit configured to convert a spatial intensity distribution of an X-ray which has passed through a subject into two-dimensional image data;
a wireless base station configured to perform wireless communication with the X-ray image receiving unit; and
a control unit configured to limit a communication possible range of the wireless base station based on an X-ray source irradiation direction.

11. The X-ray imaging system according to claim 10, wherein the control unit is configured to limit the communication possible range of the wireless base station in a case where the X-ray image receiving unit is controlled to convert a spatial intensity distribution of an X-ray into two-dimensional image data.

12. The X-ray imaging system according to claim 10, wherein the control unit is configured to limit the communication possible range of the wireless base station when imaging by the X-ray image receiving unit is controlled with respect to the communication possible range when image data captured by the X-ray image receiving unit is communicated.

13. The X-ray imaging system according to claim 10, wherein, in a case where communication with the X-ray image receiving unit on a predetermined condition cannot be performed when the control unit limits the communication possible range of the wireless base station, a warning is displayed on a display unit.

14. A control apparatus controlling a wireless base station comprising:
a wireless base station configured to perform wireless communication with an X-ray image receiving unit; and
a control unit configured to limit a communication possible range of the wireless base station when imaging by the X-ray image receiving unit is controlled with respect to the communication possible range when image data captured by the X-ray image receiving unit is communicated.

15. The control apparatus according to claim 14, wherein the wireless base station is put on a housing of the X-ray source.

16. The control apparatus according to claim 14, wherein the communication possible range is a range where an intensity of a radio wave received by the wireless base station or the X-ray image receiving unit is equal to or greater than a predetermined value.

17. The control apparatus according to claim 14, wherein the communication possible range is a range where an amount of information correctly communicated in a given length of time is equal to or greater than a predetermined value.

18. The control apparatus according to claim 14, wherein limiting the communication possible range is to limit directivity of a radio wave of the wireless base station or the X-ray image receiving unit.

19. The control apparatus according to claim 14, wherein limiting the communication possible range is to limit a communication possible distance by lowering an intensity of a radio wave of the wireless base station or the X-ray image receiving unit.

20. A control apparatus controlling a wireless base station comprising:
a wireless base station configured to perform wireless communication with an X-ray image receiving unit; and
a control unit configured to limit a communication possible range of the wireless base station based on an X-ray source irradiation direction.

21. The control apparatus according to claim 20, wherein the control unit is configured to limit the communication possible range of the wireless base station in a case where the X-ray image receiving unit is controlled to convert a spatial intensity distribution of an X-ray into two-dimensional image data.

22. The control apparatus according to claim 20, wherein the control unit is configured to limit the communication possible range of the wireless base station when imaging by the X-ray image receiving unit is controlled with respect to the communication possible range when image data captured by the X-ray image receiving unit is communicated.

23. The control apparatus according to claim 20, wherein, in a case where communication with the X-ray image receiving unit on a predetermined condition cannot be performed when the control unit limits the communication possible range of the wireless base station, a warning is displayed on a display unit.

24. A non-transitory computer-readable storage medium storing a program causing a computer to execute a control method for a wireless base station configured to perform wireless communication with a X-ray image receiving unit, the control method comprising:

limiting a communication possible range of the wireless base station based on an X-ray source irradiation direction.

\* \* \* \* \*